(12) United States Patent
Ferguson (10) Patent No.: US 8,688,475 B2
(45) Date of Patent: Apr. 1, 2014

(54) METHOD AND SYSTEM FOR CLINICAL TRIAL COMPLIANCE

(75) Inventor: John Robert Ferguson, Concord, MA (US)

(73) Assignee: General Electric Company, Schenectady, NY (US)

( * ) Notice: Subject to any disclaimer, the term of this patent is extended or adjusted under 35 U.S.C. 154(b) by 994 days.

(21) Appl. No.: 11/595,236

(22) Filed: Nov. 10, 2006

(65) Prior Publication Data

US 2008/0114616 A1    May 15, 2008

(51) Int. Cl.
*G06Q 50/00*    (2012.01)
(52) U.S. Cl.
USPC .................................... 705/3; 705/2
(58) Field of Classification Search
USPC ....................................... 705/2, 3, 4
See application file for complete search history.

(56) References Cited

U.S. PATENT DOCUMENTS

| | | | |
|---|---|---|---|
| 5,692,125 A * | 11/1997 | Schloss et al. | ............... 705/7.16 |
| 5,991,731 A | 11/1999 | Colon et al. | |
| 5,995,937 A | 11/1999 | DeBusk et al. | |
| 6,496,827 B2 | 12/2002 | Kozam et al. | |
| 6,820,235 B1 | 11/2004 | Bleicher et al. | |
| 6,850,890 B1 * | 2/2005 | Roff | .................................. 705/4 |
| 6,879,970 B2 | 4/2005 | Shiffman et al. | |
| 6,904,434 B1 | 6/2005 | Wallach et al. | |
| 7,054,823 B1 | 5/2006 | Briegs et al. | |
| 2002/0148893 A1 * | 10/2002 | Walsh et al. | ................... 235/380 |
| 2003/0130871 A1 * | 7/2003 | Rao et al. | ........................... 705/2 |
| 2006/0161457 A1 * | 7/2006 | Rapaport et al. | ................... 705/2 |
| 2006/0277071 A1 * | 12/2006 | Shufeldt | ........................... 705/3 |
| 2008/0109258 A1 * | 5/2008 | Kirschenbaum et al. | ......... 705/3 |

* cited by examiner

*Primary Examiner* — John Pauls
*Assistant Examiner* — Edward Winston, III
(74) *Attorney, Agent, or Firm* — Hanley, Flight & Zimmerman, LLC (57) ABSTRACT

A method for improving clinical trial compliance for a business entity using a computer system including a database is provided. The method includes selecting a clinical trial facility and at least one clinical trial subject, creating a clinical trial protocol including at least medical service cost data for an insurance company and a clinical trial sponsor, establishing a second subsystem including a software application that schedules appointments, establishing a third subsystem including a software application that that generates invoices, storing the clinical trial protocol, the second subsystem and the third subsystem in the database. The method also includes providing communication means between the clinical trial protocol, the second subsystem and the third subsystem, performing a medical service on the at least one clinical trial subject and determining a corresponding medical service cost, and comparing the medical service cost against the clinical trial protocol to determine whether the medical service cost is included in the clinical trial protocol.

21 Claims, 7 Drawing Sheets

METHOD AND SYSTEM FOR CLINICAL TRIAL COMPLIANCE

BACKGROUND OF THE INVENTION

This invention relates generally to clinical trial compliance and, more particularly, to methods and systems for enhancing clinical trial compliance during a clinical trial.

Clinical trials are research studies designed to answer specific questions about new medical therapies or new ways of using known therapies. Generally, clinical trials are used to determine whether new drugs or treatments are safe and effective. Usually, individuals volunteer to become subjects who participate in clinical trials. At least some subjects may have health care insurance that is generally responsible for paying their medical service costs. However, should a patient become a clinical trial subject, certain medical services associated with the trial are reimbursed by a sponsor. For example, in a pharmaceutical clinical trial a pharmaceutical sponsor may agree to pay for drugs administered during a trial.

Full payment for clinical trial medical services may be collected from a subject's insurance or from the sponsor, but not both. Some known medical system software applications may send invoices to both the subject's insurance company and the sponsor—for the same medical service. Should fees ultimately be collected from both sources for the same service, the hospital or physician conducting the trial is considered non-compliant and may be subject to financial penalties levied by government agencies.

Consequently, hospitals and physicians involved with a clinical trial may have to make excessive write-offs to ensure billing compliance. Additionally, due to their software applications, they may be unaware that a patient is also a clinical trial subject, may encounter delays and errors in billing and collections for clinical trial activity, and may not consider scheduling subjects according to pre-defined protocols.

BRIEF DESCRIPTION OF THE INVENTION

In one aspect, a method for improving clinical trial compliance for a business entity using a computer system including a database is provided. The method includes selecting a clinical trial facility and at least one clinical trial subject, creating a clinical trial protocol including at least medical service cost data for an insurance company and a clinical trial sponsor, establishing a second subsystem including a software application that schedules appointments, establishing a third subsystem including a software application that that generates invoices, storing the clinical trial protocol, the second subsystem and the third subsystem in the database. The method also includes providing communication means between the clinical trial protocol, the second subsystem and the third subsystem, performing a medical service on the at least one clinical trial subject and determining a corresponding medical service cost, and comparing the medical service cost against the clinical trial protocol to determine whether the medical service cost is included in the clinical trial protocol.

In another aspect, a system for enhancing clinical trial revenue for a business entity using a computer system including a database is provided. The system includes a clinical trial facility and at least one clinical trial subject, and a clinical trial protocol including at least medical service cost data and a schedule of appointments that the at least one clinical trial subject experiences during a clinical trial. The system also includes a second subsystem including a software application that schedules appointments and a third subsystem including a software application that generates invoices. The clinical trial protocol, the second subsystem and the third subsystem communicate with each other and the at least one clinical trial subject is monitored to verify that the at least one clinical trial subject adheres to the schedule of appointments.

In yet another aspect, an apparatus for improving clinical trial compliance for a business entity is provided. The apparatus includes a database for storing information and a computer coupled to the database. The computer is programmed to store in the database a clinical trial protocol, a second subsystem and a third subsystem, the protocol includes at least medical service cost data for an insurance company and a clinical trial sponsor, the second subsystem includes a software application that schedules appointments, and the third subsystem includes a software application that generates invoices. The computer is also programmed to provide communication between the clinical trial protocol, the second subsystem and the third subsystem, and compare a medical service cost for a medical service performed on the clinical trial subject during a clinical trial against the clinical trial protocol to determine whether the medical service cost is included in the clinical trial protocol.

DETAILED DESCRIPTION OF THE INVENTION

The methods and systems described herein facilitate enhancing billing compliance and maximizing clinical trial revenue. The methods and systems described herein are believed to be applicable to many different businesses for billing compliance and maximizing revenue. The example embodiment described herein is the medical clinical trial business. Although the medical clinical trial business is the example business described herein, the invention is in no way limited to the medical clinical trial business.

Exemplary embodiments of systems and processes that facilitate integrated network-based electronic verification of proper clinical trial billing of proper clinical trial subject participation are described below in detail. The systems and processes facilitate, for example, electronic submission of trial subject information using an HCTT (Hospital Clinical Trial Thread) system. A technical effect of the systems and processes described herein include at least one of permitting a hospital to manage, track and report clinical trial appointments, services and medical expenditures for each clinical trial subject. More specifically, in the example embodiment, a hospital that is engaged in the business of conducting medical clinical trials, including but not limited to, pharmaceutical trials, utilizes the methods and systems of the example embodiment to manage and track clinical trial subjects such that the trial results are more accurate. Additionally, by ensuring proper parties pay for the medical costs incurred by the hospital, hospitals are compliant because double billing does not occur.

In the exemplary embodiment, the HCTT system is utilized to collect, track and display clinical trial participant data such as, but not limited to, adverse events, appointment attendance and accurate identification of expenditures for clinical trial treatments and services. At least some of the parties that may be involved in these systems and processes include clinical trial subjects, physicians, clinical trial facilities, sponsors and researchers. The term clinical trial subjects refers to the individuals who voluntarily agree to take part in clinical trials. Physicians may provide medical services to the clinical trial subjects during the clinical trial. Clinical trial facilities include and entity that may provide the facilities for conducting a clinical trial, such as, but not limited to, hospitals and physicians' offices. Sponsors are usually medical device or pharmaceutical companies that initiate the trial and provide the treatments given to the clinical trial subjects. Researchers are the scientists conducting the clinical trial and determining the results for the sponsor.

In the example embodiment, users of the HCTT system are able to perform many tasks, such as, but not limited to, accurately determining responsible parties for medical service reimbursement, monitor unscheduled medical appointments, determine adverse events and verify subject appointment attendance. In the example embodiment, the HCTT system includes a first subsystem, a second subsystem and a third subsystem.

The first subsystem defines a clinical trial protocol. The protocol is a set of standards or rules established by the researchers for a particular medical clinical trial. More specifically, the protocol may include information such as, but not limited to, personal data for each subject, treatment, appointment schedule, insurance information and services that are reimbursable by the clinical trial sponsor.

Personal subject data may include information such as, but not limited to, the subject's age, height, weight, name, address, phone number, insurance information, allergies, current maladies and current medications. It should be appreciated that protocols may contain any information regarding a subject that is necessary for conducting the particular clinical trial.

In the example embodiment, the treatment is the medical therapy required for conducting the medical clinical trial. For example, in a pharmaceutical trial, the treatment may include administering a given dosage of an experimental drug once a day or several times a day. The number of times per day is dictated by the protocol. Furthermore, the treatment is generally administered according to a predetermined schedule of appointments. The appointment schedule is for visits and services that a clinical trial subject experiences during the course of the clinical trial. If the schedule of appointments is not strictly followed, the clinical trial results may be compromised. Consequently, when a clinical trial subject does not appear for an appointment, he may be removed from the clinical trial. However, if the clinical trial protocol allows, appointments may be rescheduled without effecting the trial results.

The protocol also identifies particular medical services and who is responsible for paying associated costs while the subject is participating in the clinical trial. More specifically, the protocol establishes whether a subject's insurance or the sponsor is responsible for a particular medical service. Moreover, the protocol may determine whether both the insurance and the sponsor each pay for part of a medical service cost without double billing. For example, a person suffering from cancer may receive chemotherapy or other standard of care prior to participating in a clinical trial. During the clinical trial the subject's cancer treatments would be paid for by his insurance, not by the clinical trial sponsor. Should the clinical trial involve an experimental cancer therapy, or other therapy unrelated to the standard of care, the sponsor would pay.

It should be appreciated that each clinical trial includes a different protocol that is tailored to the characteristics of the particular trial. It should also be appreciated that treatments administered during clinical trials may be any kind of medical treatment or therapy.

The second subsystem is a known business software application used for scheduling appointments. For example, Version 4.2 of Flowcast may be used for scheduling appointments. It should be appreciated that other embodiments may use any software application capable of scheduling appointments as described herein. Further, it should be appreciated that although the example embodiment describes the second subsystem as an appointment scheduling software application, other embodiments may include any software application representing any aspect of clinical trials as the second subsystem. For example, the second subsystem may also be a software application for admitting patients or for altering collection policies.

The third subsystem includes a known business solution billing software that generates bills, or invoices, for each subject participating in a clinical trial. It should be appreciated that other embodiments may use any software application capable of generating bills, or invoices, as described herein. Further, it should be appreciated that although the example embodiment describes the third subsystem as a billing software application, other embodiments may include any software application representing any aspect of clinical trials as the third subsystem. For example, the third subsystem may also be a software application for admitting patients or for altering collection policies.

It should be appreciated that although the example discussed above is from the medical clinical trial business, the HCTT system may be used in any other business or field of endeavor involving subject monitoring and compliant billing. However, it should be further appreciated that other businesses or organizations may define a different set of criteria for other protocols and that for each business clinical trial protocols will be different.

In one embodiment, a computer program is provided, and the program is embodied on a computer readable medium and utilizes a Structured Query Language (SQL) with a user interface for administration and an interface for standard input and generating reports. In an exemplary embodiment, the system is run on a business-entity intranet. In a further exemplary embodiment, the system is being run in a Windows® NT environment (Windows is a registered trademark of Microsoft Corporation, Redmond, Wash.). The application is flexible and designed to run in various different environments without compromising any major functionality.

The systems and processes are not limited to the specific embodiments described herein. In addition, components of each system and each process can be practiced independently and separately from other components and processes described herein. Each component and process also can be used in combination with other assembly packages and processes.

In the example embodiment, an interface records and tracks data generated for each subject during a clinical trial and provides accurate and proper billing. The data are stored electronically in the HCTT system as part of the clinical trial documentation. A method for facilitating reducing double billing insurance companies and sponsors is provided, so that clinical trial companies are in compliance. Furthermore, the exemplary embodiment provides a method for improving the accuracy of clinical trial results by identifying trial subjects that should be removed from the trial and enhances revenue for clinical trial businesses or hospitals. Consequently, clinical trial businesses will enjoy a higher level of compliance, will generate more accurate clinical trial results and will increase revenue.

Figure 1:
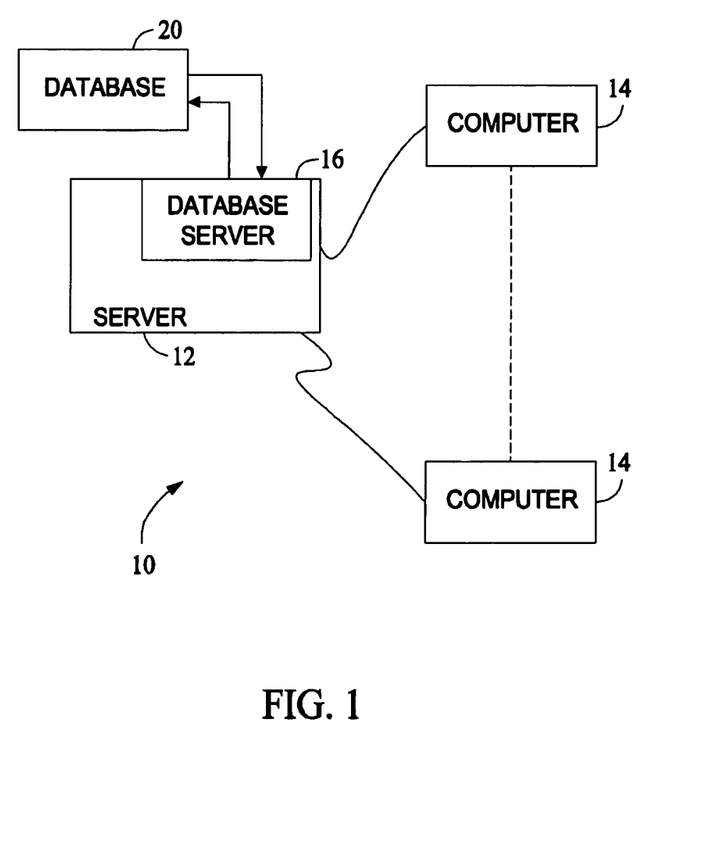
FIG. 1 is a simplified block diagram of an HCTT system in accordance with one embodiment of the present invention.

FIG. 1 is a simplified block diagram of a Hospital Clinical Trial Thread (HCTT) 10 system including a server system 12, and a plurality of client sub-systems, also referred to as client systems 14, connected to server system 12. Computerized modeling and grouping tools, as described below in more detail, are stored in server 12 and can be accessed by a requester at any one of computers 14. A database server 16 is connected to a database 20 containing information on a variety of matters, as described below in greater detail. In one embodiment, centralized database 20 is stored on server system 12 and can be accessed by potential users at one of client systems 14 by logging onto server system 12 through one of client systems 14. In an alternative embodiment, database 20 is stored remotely from server system 12 and may be non-centralized.

Figure 2:
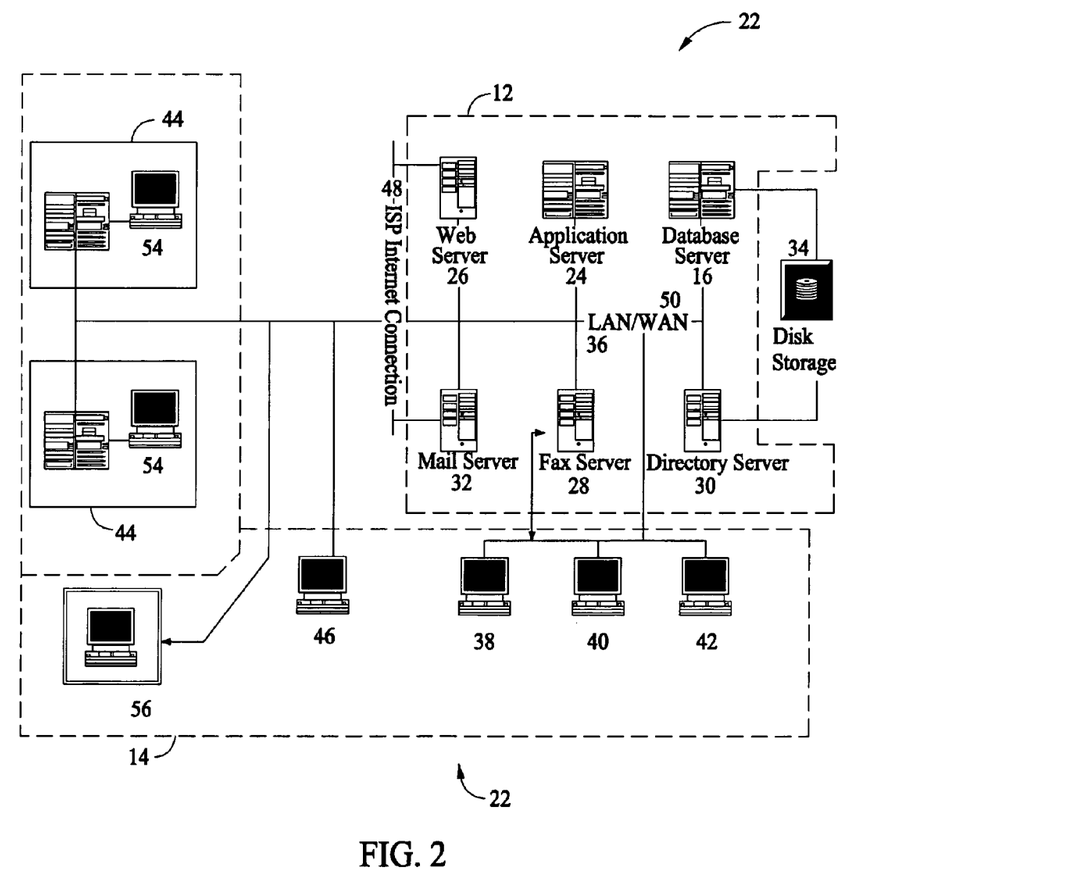
FIG. 2 is an expanded version block diagram of an example embodiment of a server architecture of the HCTT system.

FIG. 2 is an expanded block diagram of an exemplary embodiment of a server architecture of a HCTT. Components in system 22, identical to components of system 10 (shown in FIG. 1), are identified in FIG. 2 using the same reference numerals as used in FIG. 1. System 22 includes server system 12 and client systems 14. Server system 12 further includes database server 16, an application server 24, a fax server 28, a directory server 30, and a mail server 32. A disk storage unit 34 is coupled to database server 16 and directory server 30. Servers 16, 24, 26, 28, 30, and 32 are coupled in a local area network (LAN) 36. In addition, a system administrator's workstation 38, a user workstation 40, and a supervisor's workstation 42 are coupled to LAN 36.

Each workstation, 38, 40, and 42 is a personal computer. Although the functions performed at the workstations typically are illustrated as being performed at respective workstations 38, 40, and 42, such functions can be performed at one of many personal computers coupled to LAN 36. Workstations 38, 40, and 42 are illustrated as being associated with separate functions only to facilitate an understanding of the different types of functions that can be performed by individuals having access to LAN 36.

Server system 12 is configured to be communicatively coupled to various individuals, including employees 44 and to third parties, e.g., clients/customers, 46 using LAN 36. The communication in the exemplary embodiment is illustrated as being performed using LAN 36, however, any other wide area network (WAN) and internet type communication can be utilized in other embodiments, i.e., the systems and processes are not limited to being practiced using LAN 36. In addition, and rather than LAN 36, wide area network 50 or the internet could be used in place of LAN 36.

In the example embodiment, any authorized individual having a workstation 54 can access system 22. At least one of the client systems includes a manager workstation 56. Workstations 54 and 56 are personal computers configured to communicate with server system 12. Furthermore, fax server 28 communicates with client systems, including a client system 56 using a telephone link. Fax server 28 is configured to communicate with other client systems 38, 40, and 42 as well.

Figure 3:
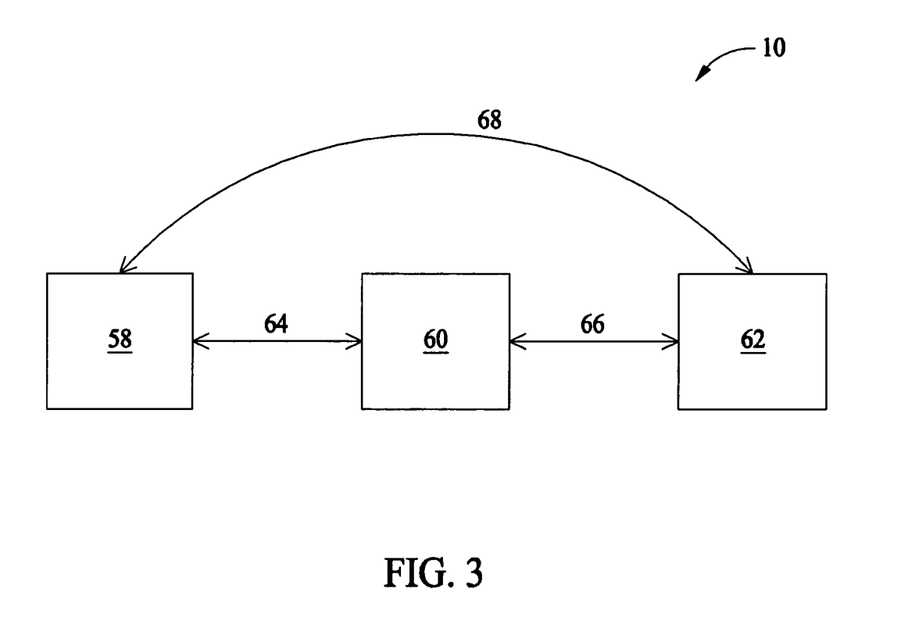
FIG. 3 is a schematic block diagram showing communication between subsystems.

FIG. 3 is a schematic block diagram illustrating the three subsystems of the exemplary embodiment. More specifically, system 10 includes a first subsystem 58, a second subsystem 60 and a third subsystem 62. Subsystem 58 is also the clinical trial protocol 59. Subsystems 58 and 60 communicate over a communications link 64. Information may flow from first subsystem 58 to second subsystem 60 and from second subsystem 60 to first subsystem 58. Subsystems 60 and 62 communicate over a communications link 66. Information may also flow in two directions. That is, information may flow from second subsystem 60 to third subsystem 62 and information may flow from third subsystem 62 to second subsystem 60. Subsystems 58 and 62 communicate over a communications link 68. Similar to communications links 64 and 66, information may flow in two directions over link 68. That is, information may flow from first subsystem 58 to third subsystem 62 and information may flow from third subsystem 62 to first subsystem 58. It should be appreciated that subsystems 58, 60 and 62 are stored on database 20. The software application that provides links 64, 66 and 68 serve as threads that tie the subsystems 58, 60 and 62 together as the HCTT system.

Figure 4:
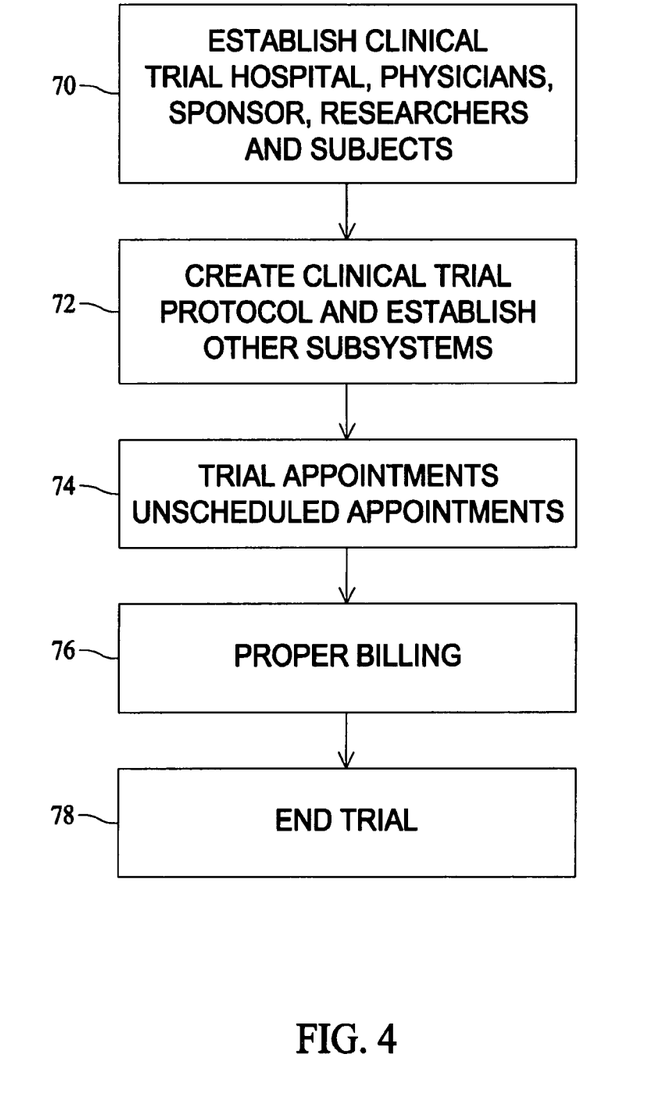
FIG. 4 is a flowchart illustrating exemplary processes utilized in HCTT.

FIG. 4 is a flowchart illustrating exemplary processes used by the HCTT system during a clinical trial. For the HCTT system, clinical trials begin 70 by identifying the medical treatment, sponsoring company, hospital, physicians, subjects and researchers. Next, the first subsystem 58, or clinical trial protocol 59, is created 72 by the researchers and is stored in the HCTT system, and the second 60 and third 62 subsystems are established.

After establishing these subsystems, 58, 60 and 62 the subject's appointment attendance and unscheduled medical visits are monitored 74. Next, after a subject has an unscheduled medical visit, the HCTT system determines whether the cause of the visit is related to the clinical trial, and if so, who is responsible for payment 76. The trial ends 78 by providing the researchers with the data generated during the trial.

Figure 5:
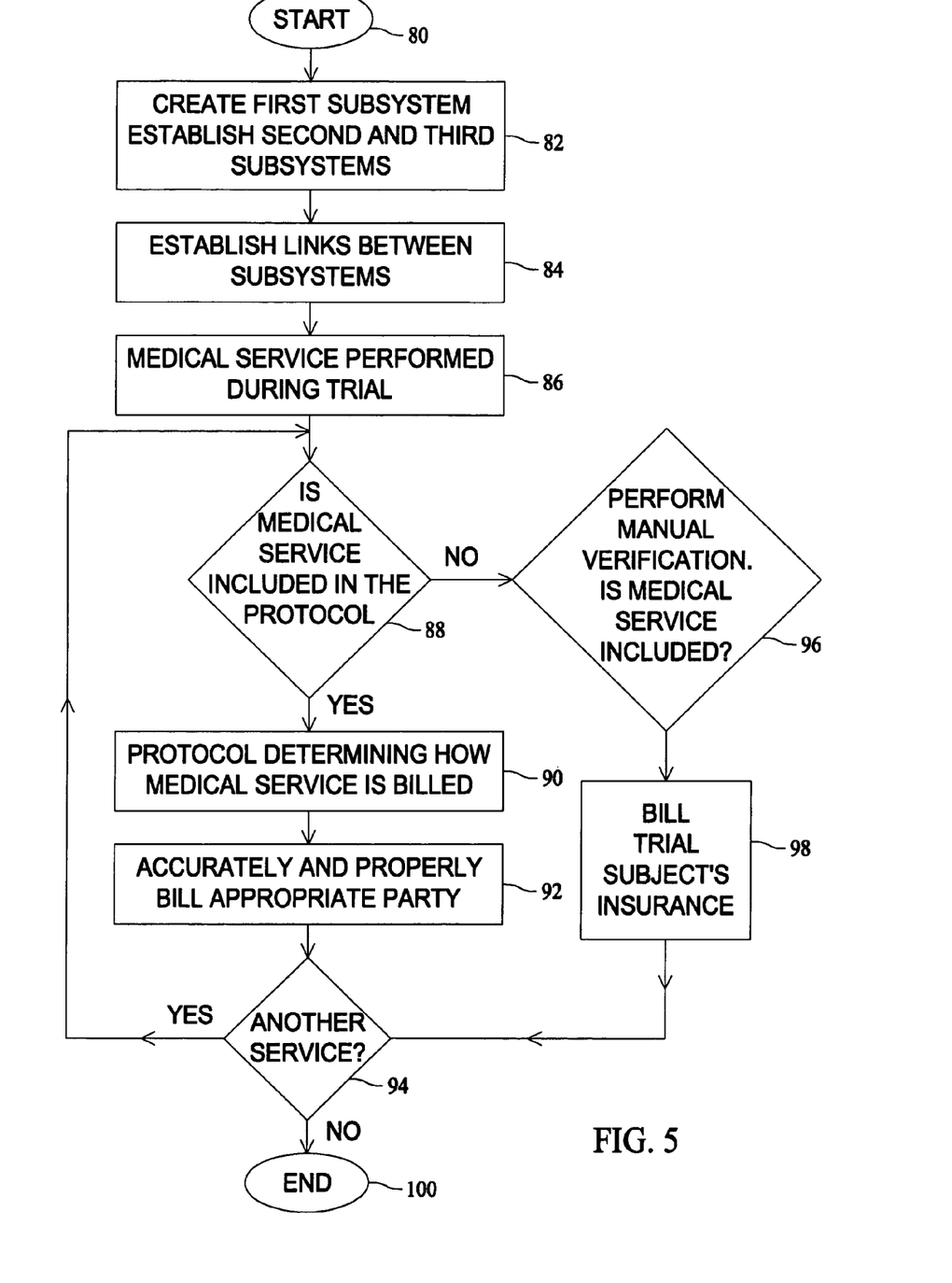
FIG. 5 is a more detailed flowchart illustrating exemplary processes utilized in the HCTT system.

FIG. 5 is a flowchart illustrating one of the exemplary processes of FIG. 4 in much greater detail. The technical effect of the processes and systems described herein is achieved when a clinical trial subject receives medical care as part of the trial or otherwise. After starting 80, subsystem 58 is created 82 and subsystems 60 and 62 are established. Next, communication links 64, 66 and 68 are created 84 between respective subsystems 58, 60 and 62. During the clinical trial, medical services associated with the trial are provided to the subjects 86. The medical service costs are then compared 88 against the insurance and sponsor reimbursement information contained in protocol 59 to determine whether the particular medical cost is included in protocol 59. The following discussion describes operation processing to step 90, then describes operation proceeding to step 96.

If the medical service cost is included in protocol 59, protocol 59 also determines 90 whether the insurance company, the sponsor, or both are responsible for reimbursing the medical service costs. If the sponsor is responsible, the insurance is automatically super-ceded. If both the sponsor and insurance company are responsible, protocol 59 determines the percentage of the total cost to be reimbursed by the insurance and by the sponsor, respectively, so that double billing does not occur. After determining proper billing for a medical service, appropriate invoices are provided 92 to the insurance company and/or the sponsor. If another medical service was provided to the subject 94, it is compared against protocol 59 and processed as described above. Otherwise, operation ends 100.

If the service cost does not appear to match protocol 59, the service cost is manually compared 96 against protocol 59 to verify it is not included in protocol 59. This facilitates avoiding billing errors. If non-inclusion in protocol 59 is verified, an invoice is sent 98 to the clinical trial subject's insurance company for reimbursement. If another medical service was provided to the subject 94, the service cost is compared 88 against protocol 59 and processed as described above. Otherwise, operation ends 100.

Figure 6:
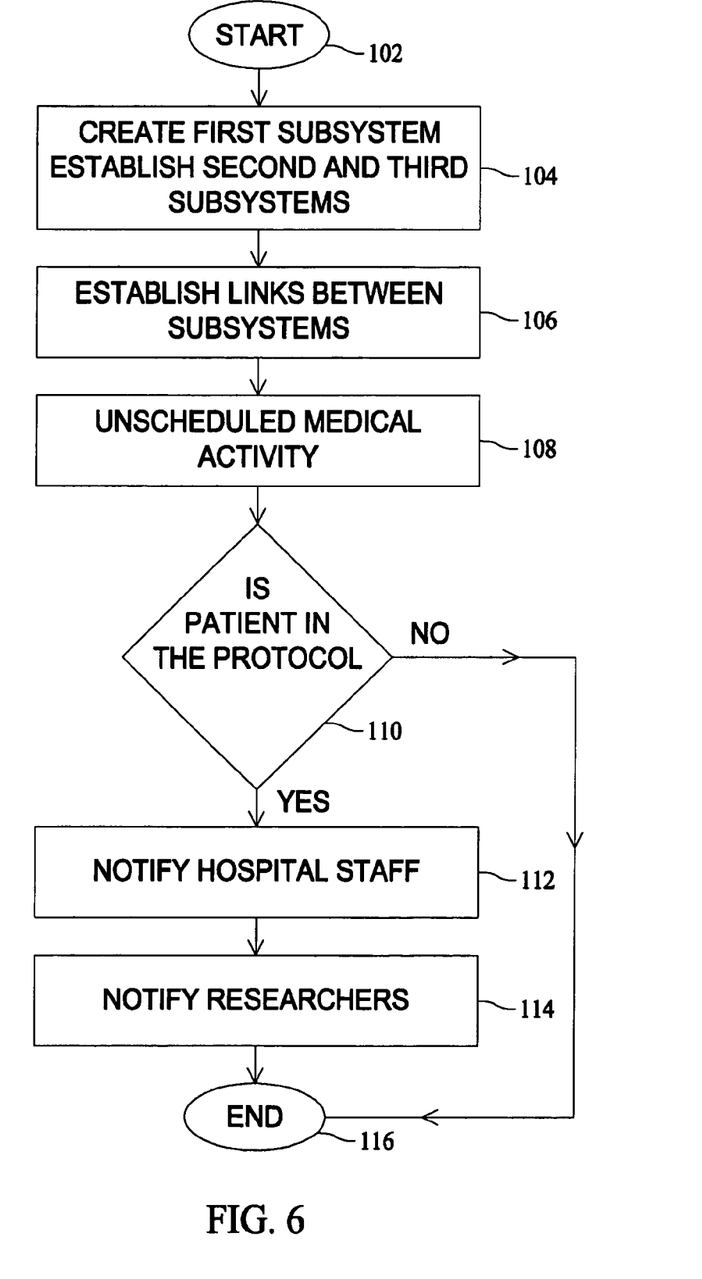
FIG. 6 is another more detailed flowchart illustrating exemplary processes utilized in the HCTT system.

FIG. 6 is a flowchart illustrating another exemplary process of FIG. 4 in much greater detail. Similar to the flowchart of FIG. 5, after starting 102 operation, subsystem 58 is created 104, subsystems 60 and 62 are established 104, and communication links 64, 66 and 68 are established 106 between respective subsystems 58, 60 and 62. During the clinical trial, a clinical trial subject may be admitted into a hospital emergency room, or other medical facility, 108 as a patient. If the subject is treated at a hospital different than the clinical hospital, or clinical trial facility, the patient should notify the non-clinical hospital that he is a clinical trial subject. The non-clinical hospital will then notify the clinical trial hospital and the trial researchers, and advise them that a clinical trial subject is being treated at a non-clinical hospital. Health care professionals at the non-clinical hospital will administer care that does not jeopardize the subject's health.

If the emergency room is associated with the clinical hospital, the HCTT system determines whether the patient is included in protocol 59. More specifically, the personal information of the emergency room patient is compared 110 against protocol 59. If the emergency room patient is not in protocol 59 then operation ends 116. However, if the emergency room patient is included in protocol 59, the hospital health care professionals are notified 112 that the emergency room patient is also a clinical trial subject. Upon notifying hospital health care professionals that the emergency room patient is also a clinical trial subject, the health care professionals understand that normal standards of care may jeopardize the subject's health. Moreover, normal standards of care may also jeopardize the subject's continued participation in the clinical trial. Consequently, the hospital health care professionals determine which standards of care may jeopardize the subject's health, and participation in the trial, and do not administer these standards of care. Furthermore, upon identifying the emergency room patient as a clinical trial subject, the clinical trial researchers are notified 114 so they can determine whether protocol 59 has been broken or if an adverse event has occurred.

Protocol 59 is considered broken when an event occurs that is not according to the standards established in protocol 59. When protocol 59 has been broken the clinical trial subject should be removed from the trial. A subject who has broken protocol 59 is removed because they may constitute inaccurate data. Thus, because the clinical trial data only includes subjects who strictly followed the established protocol 59, the clinical trial data is more accurate.

An adverse event occurs when a trial subject suffers a side effect due to the clinical trial treatment or therapy. An adverse event provides information for the researchers to incorporate in their conclusions regarding the clinical trial. After determining whether protocol 59 has been broken or whether an adverse event has occurred, operation ends 116.

Figure 7:
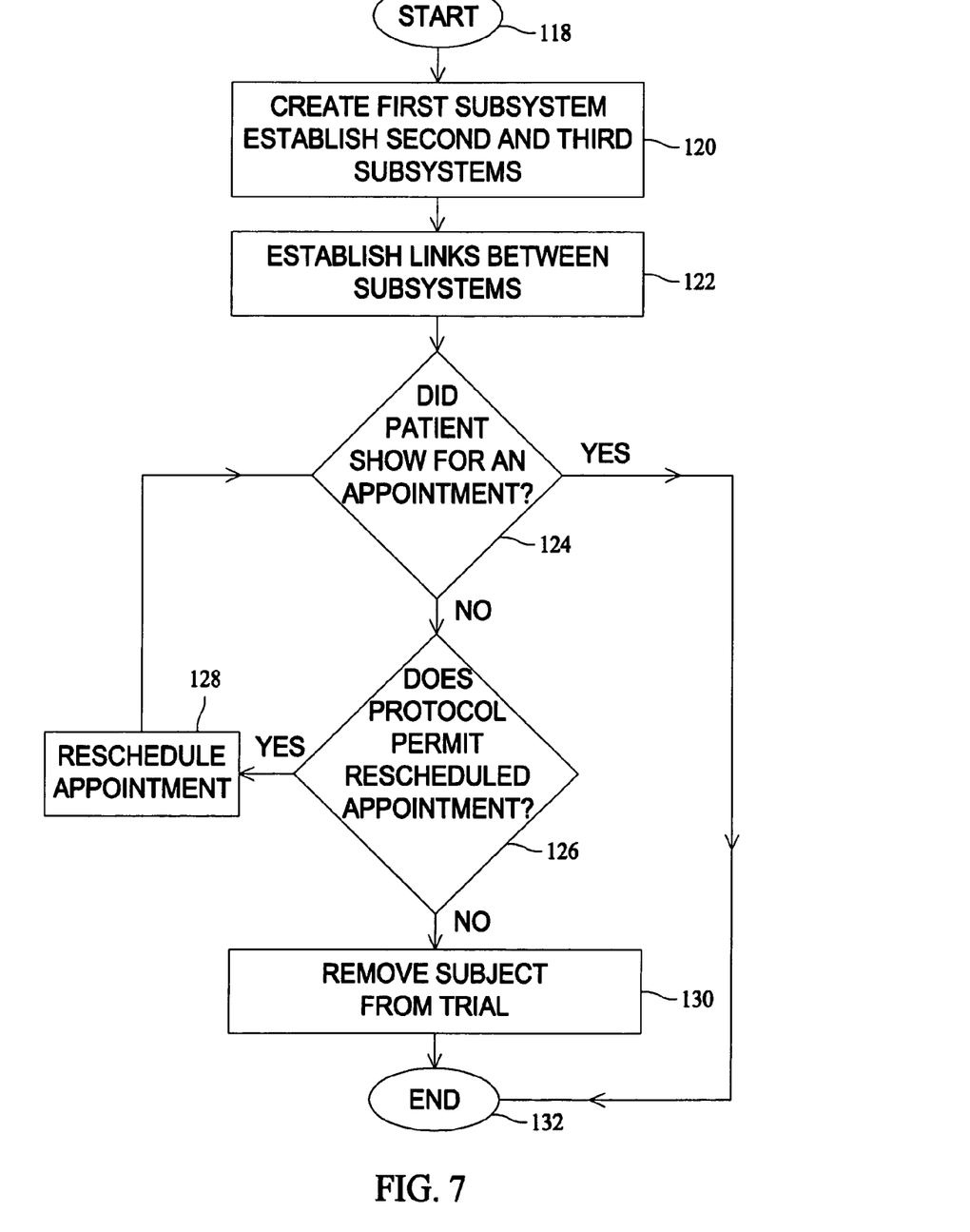
FIG. 7 is yet another more detailed flowchart illustrating exemplary processes utilized in the HCTT system.

FIG. 7 is a flowchart illustrating yet another exemplary process of FIG. 4 in much greater detail. Similar to flowcharts 5 and 6, after starting operation 118 subsystem 58 is created 120, subsystems 60 and 62 are established 120, and communication links 64, 66 and 68 are established 122 between respective subsystems 58, 60 and 62. The clinical trial protocol 59 defines a series of appointments for each clinical trial subject. When subjects arrive at the hospital, or clinical trial facility, for an appointment, they may be required to complete paperwork or other administrative processes. These appointments are designed by the trial researchers to provide the best and most reliable clinical trial results. Consequently, trial subjects should strictly adhere to the appointment schedule or risk being removed from the trial.

Clinical trial facilities, or hospitals, conducting clinical trials for sponsoring companies are compensated in stages for each clinical trial subject. For example, the hospital may receive a total of one hundred dollars for each trial subject that successfully completes the trial in strict compliance with the established protocol 59. Generally, the hospital receives an initial twenty-five percent payment, or twenty-five dollars, for each person enlisted in the initial stage as a clinical trial subject. For each trial subject that is still participating in the trial at the fifty percent stage, the hospital receives another twenty-five percent payment, or twenty-five dollars. Finally, for each trial subject that participates through the last stage of the trial, that is, to one hundred percent completion, the hospital receives a final fifty percent payment, or fifty dollars. Consequently, the hospital has an incentive to keep each trial subject participating in the trial for as long as possible.

Thus, the exemplary process illustrated in FIG. 7 provides a system for verifying that trial subjects strictly adhere to the appointment schedule by monitoring trial subject's appointments 124. Specifically, when a patient arrives for a scheduled appointment 124, an operator manually enters data into the HCTT system confirming attendance. If a trial subject shows-up for an appointment 124, operation ends 132. However, if a trial subject does not show-up for an appointment 124, the clinical trial researchers are notified immediately so the subject may be rescheduled and continue participating in the trial. Protocol 59 determines whether or not an appointment may be rescheduled 126. If so, the appointment is rescheduled 128 and the system continues to monitor appointments 124. Otherwise, if the protocol does not permit rescheduling 126, it is considered a breach of clinical trial protocol 59 and the trial subject is removed 130 from the clinical trial. By immediately notifying the clinical research staff, the HCTT system facilitates maximizing the number of clinical trial subjects and maximizing their clinical trial participation time, thus enhancing revenue received during the trial. Operation then ends 132.

While the invention has been described in terms of various specific embodiments, the description of the various embodiments is illustrative only and is not to be construed as limiting the invention. Various other modifications and changes may occur to those skilled in the art will without departing from the spirit and scope of the invention.

What is claimed is:

1. A method for improving clinical trial compliance for a business entity, the method comprising:

creating a clinical trial protocol associated with a clinical trial that includes information associating one or more medical services and their respective cost data with an insurance company and a clinical trial sponsor, a schedule of appointments of medical services included in the clinical trial, information identifying which appointments in the schedule of appointments are permitted to be rescheduled, and information identifying one or more patients as clinical trial subjects, the clinical trial protocol established as a first subsystem;

establishing a second subsystem including a software application that schedules appointments for clinical trial subjects;

establishing a third subsystem including a software application that generates invoices for medical services provided for clinical trial subjects;

storing the clinical trial protocol, the second subsystem and the third subsystem in a database of a computer system;

providing communication means between the clinical trial protocol, the second subsystem and the third subsystem, wherein the computer system is configured to identify patients that are clinical trial subjects using the clinical trial protocol;

determining, with the computer system, that one of the one or more patients that is a clinical trial subject did not attend at least one appointment in the schedule of appointments;

determining, with the computer system, whether the clinical trial protocol permits rescheduling of appointments;

removing, with the computer system, the one of the one or more patients who did not attend the at least one appointment from the clinical trial when the clinical trial protocol does not permit rescheduling of appointments or keeping the one of the one or more patients as a clinical trial subject if the clinical trial protocol does permit rescheduling of appointments;

performing a particular medical service during the clinical trial on one of the one or more patients that is a clinical trial subject and determining a corresponding medical service cost;

comparing the particular medical service against the clinical trial protocol to determine whether the particular medical service is included in the clinical trial protocol;

generating an invoice, using the third subsystem, directed to (1) the insurance company to reimburse at least a portion of the medical service cost when the particular medical service is identified in the clinical trial protocol as associated with the medical service cost data for the insurance company or (2) the clinical trial sponsor to reimburse at least a portion of the medical service cost when the particular medical service is identified in the clinical trial protocol as associated with the medical service cost data for the clinical trial sponsor.

2. The method of claim 1 further comprising verifying that the medical service cost is not included in the clinical trial protocol by manually comparing the medical service cost against the clinical trial protocol when the computer system determines that the medical service cost is not included in the clinical trial protocol.

3. The method of claim 2 further comprising generating and sending an invoice to the insurance company upon verification that the medical service cost is not included in the clinical trial protocol.

4. The method of claim 1 wherein comparing the medical service cost against the clinical trial protocol further comprises determining whether at least one of the insurance company or the clinical trial sponsor is responsible for reimbursing the medical service cost.

5. The method of claim 4 further comprising sending the invoice to at least one of the insurance company or the clinical trial sponsor.

6. The method of claim 1 wherein creating a clinical trial protocol comprises creating clinical trial subject personal data.

7. The method of claim 1 further comprising monitoring for unscheduled clinical trial subject medical visits.

8. The method of claim 1 further comprising rescheduling, with the computer system, one of the scheduled appointments when it is determined that the clinical trial protocol permits rescheduling of appointments.

9. A system for enhancing clinical trial revenue for a business entity, the system comprising a computer system, wherein the computer system comprises:

a clinical trial protocol associated with a clinical trial that comprises information associating one or more medical services and their respective cost data with an insurance company and a clinical trial sponsor, a schedule of appointments of medical services included in the clinical trial, information identifying which appointments in the schedule of appointments are permitted to be rescheduled, and information identifying one or more patients as clinical trial subjects, the clinical trial protocol established as a first subsystem;

a second subsystem comprising a software application that schedules appointments for clinical trial subjects; and a third subsystem comprising a software application that generates invoices for medical services provided during a clinical trial for clinical trial subjects, wherein the clinical trial protocol, the second subsystem and the third subsystem are configured to communicate with each other and wherein the computer system is configured to:

identify patients that are clinical trial subjects using the clinical protocol;

determine that one of the one or more patients that is a clinical trial subject did not attend at least one appointment in the schedule of appointments;

determine whether the clinical trial protocol permits rescheduling of appointments;

upon a determination that the clinical trial protocol does not permit rescheduling of appointments, remove the one of the one or more patients who did not attend the at least one appointment from the clinical trial, or upon a determination that the clinical trial protocol does permit rescheduling of appointments, keeping the one of the one or more patients as a clinical trial subject;

compare a particular medical service that has been performed during the clinical trial on one of the one or more patients that is a clinical trial subject against the clinical trial protocol to determine whether the particular medical service is included in the clinical trial protocol; and generate an invoice directed to (1) the insurance company to reimburse at least a portion of a medical service cost when the particular medical service is identified in the clinical trial protocol as associated with the medical service cost data for the insurance company or (2) the clinical trial sponsor to reimburse at least a portion of the medical service cost when the particular medical service is identified in the clinical trial protocol as associated with the medial service cost data for the clinical trial sponsor.

10. The system of claim 9, wherein the computer system is further configured to reschedule one of the scheduled appointments, upon a determination that the clinical trial protocol permits rescheduling of appointments.

11. The system of claim 9 wherein unscheduled medical visits of the at least one clinical trial subject are monitored.

12. The system of claim 11 wherein when an unscheduled medical visit occurs a clinical trial researcher is notified.

13. The system of claim 12 wherein the clinical trial researcher is to determine whether an adverse event has occurred.

14. The system of claim 11 wherein when an unscheduled medical visit occurs a health care professional is notified.

15. The system of claim 14 wherein the health care professional is to administer treatment to the at least one clinical trial subject that is compatible with the clinical trial protocol.

16. An apparatus for improving clinical trial compliance for a business entity, the apparatus comprising:

a tangible machine accessible storage medium comprising instructions that, when executed, cause the machine to:

store in a database a clinical trial protocol established as a first subsystem, a second subsystem and a third subsystem, the protocol associated with a clinical trial that comprises information associating one or more medical services and their respective cost data with an insurance company and a clinical trial sponsor, a schedule of appointments of medical services included by the clinical trial, information identifying which appointments in the schedule of appointments are permitted to be rescheduled, and information identifying one or more patients as clinical trial subjects, the second subsystem comprises a software application that schedules appointments for clinical trial subjects, and the third subsystem comprises a software application that generates invoices for medical services provided for clinical trial subjects;

provide communication between the clinical trial protocol, the second subsystem and the third subsystem, wherein the computer is configured to identify patients that are clinical trial subjects using the clinical trial protocol;

determine that one of the one or more patients that is a clinical trial subject did not attend at least one appointment in the schedule of appointments;

determine whether the clinical trial protocol permits rescheduling of appointments;

upon a determination that the clinical trial protocol does not permit rescheduling of appointments, remove the one of the one or more patients who did not attend the at least one appointment from the clinical trial, or upon a determination that the clinical trial protocol does permit rescheduling of appointments, keeping the one of the one or more patients as a clinical trial subject;

compare a particular medical service performed on one of the one or more patients that is a clinical trial subject during a clinical trial against the clinical trial protocol to determine whether the particular medical service is included in the clinical trial protocol; and generate an invoice directed to (1) the insurance company to reimburse at least a portion of a medical service cost when the particular medical service is identified in the clinical trial protocol as associated with the medical service data for the insurance company or (2) the clinical trial sponsor to reimburse at least a portion of the medical service cost when the particular medical service is identified in the clinical trial protocol as associated with the medical service cost data for the clinical trial sponsor.

17. The apparatus of claim 16 wherein the clinical trial protocol further comprises clinical trial subject personal data.

18. The apparatus of claim 16 wherein the clinical trial protocol is analyzed to determine whether at least one of an insurance company or a clinical trial sponsor is responsible for reimbursing the medical service cost.

19. The apparatus of claim 16, wherein the computer is further programmed to reschedule one of the scheduled appointments, upon a determination that the clinical trial protocol permits rescheduling of appointments.

20. The apparatus of claim 16 wherein unscheduled clinical trial subject medical visits are monitored.

21. A method comprising:

generating a clinical trial protocol for a clinical trial that includes a first medical service identified as at least partially reimbursable by an insurance company and a second medical service identified as at least partially reimbursable by a clinical trial sponsor, the clinical trial protocol including a plurality of patients participating in the clinical trial;

providing a schedule of one or more appointments of medical services for a patient participating in the clinical trial including at least one of the first medical service or the second medical service;

monitoring patient attendance to determine whether the patient attends a scheduled appointment included in the clinical trial and removing the patient from the clinical trial protocol when the patient does not attached a scheduled appointment included in the clinical trial and the clinical trial protocol does not permit rescheduling of the appointment;

comparing, via a processor, when the patient has not been removed from the clinical trial, medical service cost data associated with a particular medical service performed on the patient against the clinical trial protocol, the medical service cost data including a medical service cost associated with the particular medical service;

determining whether the medical service cost data corresponds to at least one of the first medical service or the second medical service in the clinical trial protocol; and generating an invoice directed to (1) the insurance company for at least a portion of the medical service cost when the medical service cost data corresponds to the first medical service or (2) the clinical trial sponsor for at least a portion of the medical service cost when the medical service cost data corresponds to the second medical service.

* * * * *

UNITED STATES PATENT AND TRADEMARK OFFICE
CERTIFICATE OF CORRECTION

PATENT NO. : 8,688,475 B2
APPLICATION NO. : 11/595236
DATED : April 1, 2014
INVENTOR(S) : John Robert Ferguson

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1124 days.

Signed and Sealed this
Thirtieth Day of May, 2017

Michelle K. Lee
*Director of the United States Patent and Trademark Office*